United States Patent [19]

Diez et al.

[11] Patent Number: 5,276,054
[45] Date of Patent: Jan. 4, 1994

[54] SUBSTITUTED HEXAHYDROBENZOPYRAN DERIVATIVES AS ANGIOTENSIN II ANTAGONISTS

[75] Inventors: Maria T. Diez, Madrid, Spain;
Michael A. Goetz, Fanwood, N.J.;
Robert A. Giacobbe, Lavallette, N.J.;
Otto D. Hensens, Red Bank, N.J.;
Leeyan Huang, Watchung, N.J.;
Isabel Martin, Madrid, Spain; E.
Tracy T. Jones, Solana Beach, Calif.;
Siobhan Stevens-Miles, Jersey City,
N.J.; Yu L. Kong, Edison, N.J.

[73] Assignee: Merck & Co., Inc., Rahway, N.J.

[21] Appl. No.: 961,957

[22] Filed: Oct. 16, 1992

[51] Int. Cl.$^5$ .................. A61K 31/35; C07D 311/72; C07D 311/78
[52] U.S. Cl. .................... 514/455; 514/456; 549/387; 549/400
[58] Field of Search ............... 549/400, 387; 514/455, 514/456

[56] References Cited

PUBLICATIONS

Spielman, Can. J. Bot., 63, 1355-1378 (1985).

Primary Examiner—Nicky Chan
Attorney, Agent, or Firm—Valerie J. Camara; Mark R. Daniel; Joseph F. DiPrima

[57] ABSTRACT

Substituted hexahydrobenzopyran derivatives of the Formulae A, B, or C are useful as angiotensin II antagonists:

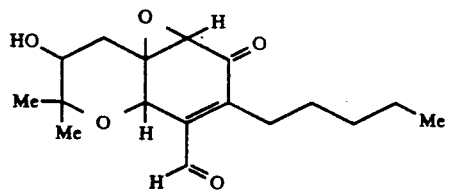

A

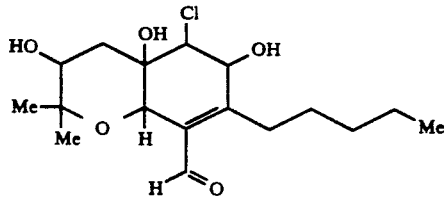

B

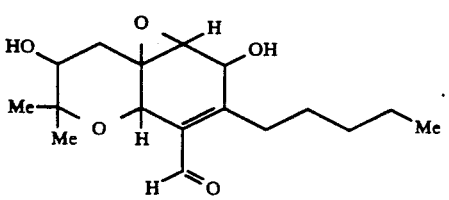

C

4 Claims, No Drawings

SUBSTITUTED HEXAHYDROBENZOPYRAN DERIVATIVES AS ANGIOTENSIN II ANTAGONISTS

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the reninangiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr. - *Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

SUMMARY OF THE INVENTION

It has now been found that three novel compounds, Compounds A, B, and C (of formulas A, B and C):

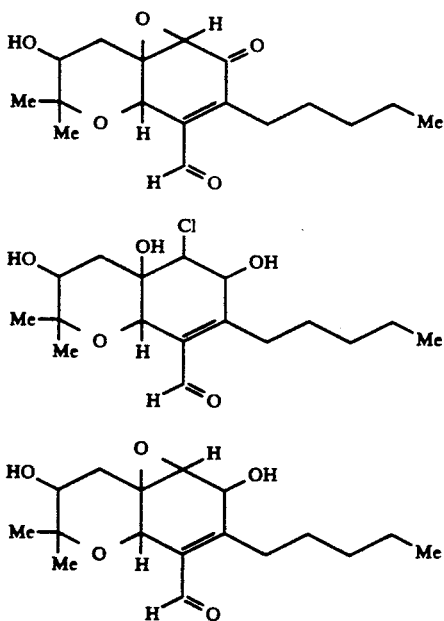

are produced by aerobic fermentation of an assimilable carbon source in a suitable nutrient medium by an unidentified species of the fungal genus Cytospora, ATCC 74091. A deposit under the Budapest Treaty of a biologically pure culture of this organism was made with the America Type Culture Collection, Rockville, Md. on Aug. 20, 1991 under accession number ATCC 74091.

The organism and its use is the subject of concurrently filed copending application Ser. No. 07/961,958.

The compounds of the present invention are angiotensin II antagonists. Moreover, it has been discovered that Compound A is particularly unique in having antagonist activity at AT-2 receptor sites, a property not possessed by most other angiotensin II antagonists. This property renders it adaptable for special applications in chemotherapy. Compositions containing the novel compounds for therapeutic use and methods of use in therapy constitute aspects of the present invention. Especially preferred are compositions for cardiovascular therapy.

The present invention also includes a process for obtaining these compounds.

DETAILED DESCRIPTION OF THE INVENTION

Strain Isolation

The producing organism of the present invention was isolated from a sample of bark of yellowish birch, *Betula alleganiensis* collected in Randolph County, West Virginia. To isolate this organism, bark discs were removed from the tree with a leather punch. Discs were approximately 1 cm in diameter and 0.3–1.0 cm thick and included an entire bark cross-section along with the vascular cambium, and sometimes a veneer of the outer xylem. Discs were soaked in 95% ethanol for 1 minute, 66% household bleach (aqueous 3.3% NaClO solution) for 5 minutes, and rinsed with 95% ethanol again for 0.5 minute prior to application to isolation media. Bark discs were applied (outer side down) to an agar medium (BBL Laboratories Mycosel Agar, Cockeysville, Md., consisting of phytone 10 g, glucose 10 g cycloheximide 0.4 g, chloramphenicol 50 mg; in 1 L distilled water) in 100 mm diameter quartered plastic petri dishes. Petri dishes were incubated at 24° C., and inspected for up to one month for the development of fungal colonies on bark discs and the agar. Hyphal fragments of colonies emerging from bark discs were transferred to slants of malt yeast extract agar.

Colonial Morphology in Agar Culture

Colonies on oatmeal agar (Difco Laboratories), 14 days, 20° C., 12 hour photoperiod (12/12 light/dark): Attaining 66–70 mm in diameter, with little development of aerial mycelium, appressed to submerged, pruinose or slightly floccose around inoculation point, dull, hyaline to pale olive when young, Buffy Olive, Light Yellowish Olive, soon dark olive to dark olivaceous black, Olive, Dark Greenish Olive, Deep Olive, Dark Grayish Olive, Dark Olive (capitalized color names from Ridgway, R., 1912, *Color Standards and Nomenclature*, Washington, D.C.) with mottled pigment development over outer third of colony, with scattered stromatic conidiomatal pustules at first white, but soon pale grayish olive to olivaceous brown, margin submerged, irregular.

Colonies on Emerson's YpSS (Difco Laboratories), 14 days, 20° C., 12 hour photoperiod: Attaining 35–45 mm in diameter, dull, aerial mycelium pruinose to downy, with scattered stromata, hyaline at margin but soon pale olive to olivaceous gray, Dark Olive-Buff, Citrine Drab, finally dark olive, Dark Greenish Olive, Dark Grayish Olive, margin minutely feathery or fimbriate.

Colonies on malt-yeast extract agar (Difco Laboratories), 14 days, 20° C., 12 hour photoperiod: Attaining 70–75 mm in diameter, shiny to moist, aerial mycelium appressed or minutely floccose around inoculation point, hyaline to greenish yellow, Yellowish Citrine, Serpentine Green, Dull Citrine, soon grayish olive to dark olive, Deep Grayish Olive, Dark Grayish Olive, Dark Olive, with scattered stromatic pustules in older portions, developing long irregular plumose branches with submerged, irregular margins.

Conidiomata scattered across colony surface, up to 1.5 mm wide, up to 2.5 mm tall, tough, stromatic, with base embedded in agar, pulvinate or hemispherical when young, becoming short cylindrical in age, with rounded apex, sometimes with subapical constrictions, with surface minutely pubescent, dehiscing irregularly in age to yield a gelatinous spore mass or spore horns, with outer cortex a textura intricata, golden to dark brown, containing a irregularly convoluted conidial chamber, which overlies or surrounds an inner cortex, with inner cortex a textura intricata to textura angularis, dark brown to black. Conidiophores arranged in a dense palisade layer, lining the internal stomatic cavity, arising from broad, short cylindrical to subglobose hyphae, branching at 3-5 levels, acropleurogenous or not, thin-walled, hyaline, smooth Conidiogenous cells enteroblastic, phialidic, cylindrical to awl-shaped, tapered to a narrow apex, $5-12 \times 1-3$ μm, with minute pore at conidiogenous locus. Conidia $3-5 \times 1-1.5$ μm cylindrical, narrowly ellipsoidal, or allantoid, exuded from conidiomata in a golden brown to yellowish olive gelatinous mass or in spore horns. Hyphae septate, branching hyaline to blackish brown, occasionally incrusted in age, up to 12 μm in diameter.

This strain can be assigned to genus Cytospora (Coelomycetes) because of its combination of the following characteristics: tough stromatic conidiomata; the production of conidiophores in a well-defined palisade layer within a convoluted, multilocular chamber, highly branched conidiophores; enteroblastic conidiogenesis; small; hyaline, more-or-less allantoid conidia; and dark mycelial colors. Members of the genus Cytospora are typical inhabitants of stems of woody plants. Several species are associated with canker and dieback diseases of woody stems. Cytospora species are often the conidial states in the life cycles of Valsa and Leucostoma species (Ascomycetes, Diaporthales), but no sexual state of this strain are observed in culture. The genus is in need of extensive revisionary studies. About 400 species have been named and nearly all species descriptions are based on anatomical characterisitics as they occur fruiting on host tissues (Sutton, B. C. (1980) *The Coelomycetes*, Commonwealth Mycological Ins. Kew; Spielman, L. J. (1985) "A Monograph of Valsa on Hardwoods in North America", Can. J. of Botany, 63: 1355-1378). The stromatic tissues, conidiophores, and conidia of ATCC 74091 are similar to many of the common Cystospora anamorphs of Valsa species described by Spielman, (1985). Because no workable identification system currently exists for these fungi in culture, and because this strain was derived from vegetative growth from bark rather than from spores produced in an identifiable fruiting structure on a host, it is impossible to determine the name of this Cytospora species.

Fermentation Conditions

Compounds of formulas A, B, and C are produced during the aerobic fermentation of suitable aqueous nutrient media under controlled conditions via inoculation with a culture of the organism ATCC 74091. The media contain sources of assimilable carbon, nitrogen, and inorganic salts.

In general, carbohydrates (for example, glucose, fructose, maltose, xylose, and the like) can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 2% to 5% by weight of the medium. These carbon sources may be used individually or combined in the medium.

Generally, many proteinaceous materials may be used as nitrogen sources for the fermentation process. Suitable nitrogen sources include, for example, yeast hydrolysates, primary yeast, soybean meal, cottonseed flour, hydrolysates of casein, cornsteep liquor, distiller's solubles or tomato paste and the like. The sources of nitrogen, either alone or in combination, are used in amounts preferably ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace elements such as cobalt, manganese, copper, molybdenun, zinc, boron, iron and magnesium.

It should be noted that the nutrient media described herein are merely illustrative of the wide variety of media which may be employed, and are not intended to be limiting.

The fermentation is carried out at temperatures ranging from about 25° C. to 35° C.; however, for optimum results it is preferable to conduct the fermentation at temperatures of from about 25° C. to 32° C. The pH of the nutrient media for growing the ATCC 74091 culture and producing Compounds A, B, and C can vary from about 6 to 8.

Although these three compounds are produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 25° C. on a shaker for up to 25 days.

The fermentation is initiated in a sterilized flask of medium via one or more stages of seed development. The nutrient medium for the seed stage may be any suitable combination of carbon and nitrogen sources, however, the preferred carbon source is glucose or hydrolyzed starch. The seed flask is shaken in a constant temperature chamber at about 28° C. for 2-4 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by extraction with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 28° C. This method of producing Compounds A, B, and C is particularly suited for the preparation of large quantities.

The product is recovered from the fermentation broth by extraction with equal volumes of solvents, generally methyl ethyl ketone, n-butanol and methanol. The extract is generally filtered to remove mycelia and then evaporated to dryness and reconstituted in solvent combinations such as 1:1 methylene chloride/methanol and isolated by several stage fractionation using thin layer chromatography (TLC) with methylene chloride/methanol with final purification and isolation on preparative HPLC and collecting bioactive fractions as hereinafter more fully described.

This invention is directed to substituted hexahydrobenzopyran derivatives of the formulas A, B, or C, which are angiotensin II antagonists and are useful in the treatment of hypertension and congestive heart failure. The compounds of the invention are also adapted to be used as ocular antihypertensives.

Additionally, pharmaceutically acceptable compositions of these novel compounds, as the sole therapeutically active ingredient and in combination with diuretics and other antihypertensive agents, including beta blockers, angiotensin converting enzyme inhibitors, calcium channel blockers or a combination thereof are disclosed and claimed. Further, methods of treating hypertension and congestive heart failure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, adapted to be employed for the relief of symptoms of anxiety and tension and in the treatment of patients with depressed or dysphoric mental states.

In addition, these compounds exhibit antidopaminergic properties and thus may be used to treat disorders that involve dopamine dysfunction such as schizophrenia. The compounds of this invention are especially useful in the treatment of these conditions in patients who are also hypertensive or have a congestive heart failure condition.

Angiotensin II (AII) is a powerful arterial vasoconstrictor, and it exerts its action by interacting with specific receptors present on cell membranes. The compounds of the present invention are competitive antagonists of AII at receptor sites. The usefulness of compounds as AII antagonists may be determined from the results of certain receptor binding assays. The initial assay is that using rat adrenal glands and the results of this assay are described herein.

Receptor assay using rat adrenal gland preparation

Adrenal membranes for the receptor assay were readied first by placing cleaned, whole adrenal glands in microcentrifuge tubes (20 glands per tube), and freezing and storing under liquid nitrogen. As needed, a microcentrifuge tube of adrenal glands was homogenized in 20 ml 50 mM Tris-HCl pH 7.7 and centrifuged at 20,000 rpm for 15 minutes at 4° C. The pellet was then resuspended in a buffer [120 mM NaCl, 10 mM $Na_2HPO_4$, 5 mM $Na_2EDTA$ and 0.1 mM phenylmethanesulfonyl fluoride (PMSF)] and centrifuged at 20,000 rpm for 15 minutes at 4° C. The last step was then repeated. The resulting pellet was resuspended in the same buffer and a 0.5 ml aliquot dispensed per microcentrifuge tube and frozen.

For the assay, the adrenal membrane preparation in one vial was resuspended in 30 ml of 100 mM Tris-HCl pH 7.4 with 5 mM $MgCl_2$, 0.2% bovine serum albumin and 0.2 mg/ml bacitracin. 200 microliters of this preparation was added to each tube containing 45 microliters of $^{125}I$-Angiotensin II to which were added 5 microliters of sample and 10 microliters of 2-butyl-4-chloro-1-((2'-(1H-tetrazol-5-yl)-1,1'-biphenyl)-4-yl)methyl-1H-imidazole-5-methanol monohydrochloride as known inhibitor of Site 1 and 1-(3-methyl-4-methoxyphenyl)-methyl-5-diphenylacetyl-4,5,6,7-tetrahydro-1H-imidazo(4,5-c)pyridine-6-carboxylic acid known inhibitor of Site 2. The tubes were then vortexed and incubated at 37° C. for 90 minutes. After the incubation period, the membranes were collected, the reaction mixture aspirated, 3–4 milliliters of 50 mM Tris-HCl pH 7.4 with 0.9% NaCl passed through the system, the mixture then filtered and the filter deposited in minivials for counting. The vials are counted with a gamma counter for one minute and percent inhibition determined from counts/min (CPM) as follows:

$$\% \text{ Inhibition} = \frac{CPM_a\text{,Control} - CMP_a\text{,Sample}}{CMP_a\text{,Control} - CMP_a\text{,Inhibitor}} \times 100$$

The $IC_{50}$ is determined by plotting percent inhibition v. concentration of compound tested. It was found that Compound A has an $IC_{50}$ of 0.5–1 µg/ml or 1–2 µM at site 2.

On positive results with rat adrenal gland assay, assays using rabbit aorta may be employed.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 mL) homogenized, and then centifuged. The mixture was filtered through a cheesecloth and the supernatant was centrifuged for 30 minutes at 20,000 rpm at 4° C. The pellet thus obtained was resuspended in 30 mL of 50 mM Tris-5 mM $MgCl_2$ buffer containing 0.2% Bovine Serum Albumin and 0.2 mg/mL Bacitracin and the suspension was used for 100 assay tubes. Samples tested for screening were done in duplicate. To the membrane preparation (0.25 mL) there was added $^{125}I$-$Sar^1Ile^8$-angiotensin II [obtained from New England Nuclear] (10 mL; 20,000 cpm) with or without the test sample and the mixture was incubated at 37° C. for 90 minutes. The mixture was then diluted with ice-cold 50 mM Tris-0.9% NaCl, pH 7.4 (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration ($IC_{50}$) of potential AII antagonist which gives 50% displacement of the total specifically bound $^{125}I$-$Sar^1Ile^8$-angiotensin II is presented as a measure of the efficacy of such compounds as AII antagonists. Compound A was found to have $IC_{50}$ of only 8 µg/ml (at site 1).

In the management of hypertension and the clinical conditions described herein, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Preferably, the dosage range will be about 2.5 to 250 mg per patient per day; more preferably about 2.5 to 75 mg per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflunisal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg), chlorothiazide (125–2000 mg), ethacrynic acid (15–200 mg), amiloride (5–20 mg), furosemide (5–80 mg), propranolol (20–480 mg), timolol maleate (5–60 mg), methyldopa (65–2000 mg), felodipine (5–60 mg), nifedipine (5–60 mg), and nitrendipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60) plus an angiotensin II antagonist of this invention (0.5–250 mg) or hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of compound or mixture of Compounds A, B, or C is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

The compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

Cognitive Function Assay

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

Anxiolytic Assay

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

Depression Assay

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

Schizophrenia Assay

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The invention is further defined by reference to the following examples, which are intended to be illustrative and not limiting.

EXAMPLE 1

Fermentation Conditions

Vegetative mycelia of the culture were prepared by inoculating 54 mL of KF seed medium (Table 1-1) in a 250 mL unbaffled Erlenmeyer flask with frozen mycelia of MF 5658, ATCC 74091. Seed flasks were incubated for 3 days at 28° C. and 75% relative humidity on a rotary shaker with a 5-cm throw at 220 rpm. Two-mL portions of the 3-day culture growth were used to inoculate 45 mL aliquots of a liquid production medium CYG-40 (Table 1-2) in 250 mL unbaffled Erlenmeyer flasks. Flasks were incubated at 25° C. and 50% relative humidity with agitation at 220 rpm on a rotary shaker with a 5-cm throw for up to 25 days. At harvest, fermentation products were extracted with 45 mL of methylethylketone per flask at 220 rpm for 1 hour at 25° C.

TABLE 1-1

| KF Seed Medium | Per L |
|---|---|
| Corn Steep Liquor | 5 g |
| Tomato Paste | 40 g |
| Oat flour | 10 g |
| Glucose | 10 g |
| Trace Element Mix | 10 mL |
| pH = 6.8 | |
| Trace Element Mix | |
| $FeSO_4.7H_2O$ | 1 g |
| $MnSO_4.4H_2O$ | 1 g |
| $CuCl_2.2H_2O$ | 25 mg |
| $CaCl_2$ | 100 mg |
| $H_3BO_3$ | 56 mg |
| $(NH_4)_6Mo_7O_{24}.4H_2O$ | 19 mg |
| $ZnSO_4.7H_2O$ | 200 mg |

TABLE 1-2

| Production Medium CYG40 | |
|---|---|
| Component | Conc. (g/L) |
| Corn Meal | 50.0 |
| Yeast Extract | 1.0 |
| Glucose | 40.0 |

EXAMPLE 2

Isolation of Compound A

A fifteen mL fermentation sample, from fermentation carried out as described in Example 1, was extracted, in succession, with equal volumes of methyl ethyl ketone, n-butanol, and methanol. The methyl ethyl ketone extract was evaporated to dryness, reconstituted in 1 mL of methylene chloride/methanol, 1:1, and fractionated by preparative thin layer chromatography (TLC) on a 20×20 cm E. Merck silica gel 60 plate (0.25 cm layer thickness) and eluted with methylene chloride/methanol, 92:8.

The single bioactive fraction thus obtained was further processed by preparative TLC on the same type of plate, this time using methylene chloride/methanol, 96:4.

Final purification and isolation of Compound A was achieved by semi-preparative high performance liquid chromatography (HPLC) on a Whatman Partisil-5 ODS-3 column (4.6 mm×25 cm) maintained at 40° C. and eluted at 1 mL/minute with 40% aqueous acetonitrile. After bioassay, the active fractions were evaporated to dryness under vacuum to yield 2 mg of Compound A whose homogeneity was ascertained by proton nuclear magnetic resonance (NMR), by TLC in several systems, and by analytical HPLC [$k'=4.25$, Whatman Partisil-5 ODS-3 column (4.6 mm×25 cm) maintained at 40° C. and eluted at 1 mL/minute with acetonitrile/water, 1:1]

EXAMPLE 3

Isolation of Compounds A, B, and C

The presence of the co-produced minor analogs (Compounds B and C) was determined when isolation of the major component A was carried out in a manner described in Example 2 on a larger scale. These analogs were not present in sufficient amounts to be readily identified by routine bioassay; rather they were recognized by their physico-chemical similarities with compound A.

Accordingly, 1.4 liters of fermentation broth, prepared as detailed in Example 1, were extracted with an equal volume of methyl ethyl ketone. Compound A was present in the extract at a concentration of 175 mg/L, as determined by high performance liquid chromatographic (HPLC) measurements.

The fermentation products were recovered and separated to obtain purified products by first extracting from the fermentation medium and thereafter employing HPLC and gel filtration techniques.

Generally, the crude methyl ethyl ketone extract was evaporated under vacuum, reconstituted in 50 ml of methylene chloride and crudely fractionated on a column of silica gel (E. M. silica gel 60, 250-400 mesh) packed and equilibrated in methylene chloride and eluted with methylene chloride containing increasing amounts of methanol. Fractions containing Compound A were then pooled, again evaporated, and further fractionated on a 100 mL silica gel column packed in methylene chloride/ethyl acetate, 90:10, and washed with the same solvent mixture, containing increasing concentrations of ethyl acetate.

Examination of fractions from the second silica gel column by HPLC revealed the presence of the major component in early eluting volumes of methylene chloride/ethyl acetate, 88:12. These were evaporated down, redissolved in methanol and further processed by gel filtration on Pharmacia SEPHADEX LH-20 gel (150 mL column, eluted with methanol, volume of elution 0.7-0.8 column volumes) and preparative HPLC [Whatman Partisil-10 ODS-3 column (20 mm×25 cm) maintained at room temperature and eluted at 8 mL/minute with 40% aqueous acetonitrile] to produce pure compound A at $k'=6.4$.

Later-eluting volumes from the second silica gel column, corresponding to methylene chloride/ethyl acetate, 1:2, washings, were recognized as containing components structurally related to the main compound by the similarities in ultraviolet absorption spectra and color reactions on TLC plates. The appropriate fractions were worked up by gel filtration on SEPHADEX LH-20 as detailed for compound A (same volume of elution). Final separation and purification of these minor analogs was achieved by preparative HPLC [Whatman Partisil-10 ODS-3 column (20 mm×25 cm) maintained at room temperature and eluted at 8 mL/minutes as follows: with 20% aqueous acetonitrile for 60 minutes, then with a 40 minute gradient from 20% to 40% aqueous acetonitrile]. The minor analogs were obtained in pure form after 50 minutes (Compound B) and 80 minutes (Compound C) of elution.

Homogeneity of the preparations was ascertained after evaporation of solvents, by proton NMR measurements, by TLC in several systems and by analytical HPLC [Whatman Partisil-5 ODS-3 column (4.6 mm×25 cm) maintained at 40° C. and eluted at 1 mL/minute with acetonitrile/water, k' for compound A: 4.25; k' for compound B: 2.4; k' for compound C: 2.91].

EXAMPLE 4

Mass Spectral Characterization

Mass spectral data were acquired for the structural analysis of Compounds A, B, and C on Finnigan-MAT models MAT212 and TSQ70B mass spectrometers.

MAT212: Electron Impact (EI) mode at 90 eV. Exact mass measurements were performed at high resolution (HR EI) using perfluorokerosene (PFK) as an internal standard.

TSQ70B: EI mode at 70 eV. Fast Atom Bombardment (FAB) mode (positive ion) employing as matrices 5:1 dithiothreitol/dithioerythritol (DTT/DTE), doped with lithium acetate and undoped. Trimethylsilyl (TMS) derivatives were prepared using a 1:1 mixture of bis(trimethylsilyl)trifluoroacetamide (BSTFA)/pyridine at 50° C.

Compound A:

The EI MS spectrum supported a MW 308 compound. The molecular formula was determined by exact mass measurement of the molecular ion:

Calculated for $C_{17}H_{24}O_5$: 308.1624. Found: 308.1634, $^{13}C$ NMR ($CD_2Cl_2$): δ14.0, 15.9, 22.7, 24.4, 27.3, 30.4, 31.9, 35.0, 60.1, 61.2, 62.8, 73.5, 77.2, 139.6, 148.7, 191.6, and 197.8.

Compound B:

The Fab MS spectra indicated a MW 346 compound; $[M+Li]^+$ at m/z 353 and $[M+H]^+$ at m/z 347 were observed. Isotope clusters for the higher mass ions in the EI MS spectrum pointed to the presence of one chlorine per molecule. The molecular formula $C_{17}H_{27}ClO_5$, was determined by exact mass measurement of $[M-H_2O]^+$.

Calculated for $C_{17}H_{25}ClO_4$: 328.1441. Found: 328.1435.

The compound formed a tri-TMS derivative.

$^{13}C$ NMR ($CD_2Cl_2/CD_3OD$): δ14.0, 22.7, 24.2, 26.6, 27.0, 30.3, 32.2, 37.6, 68.7, 71.6, 71.8, 76.9, 79.3, 83.9, 130.9, 163.0, and 191.8.

Compound C:

FAB MS results pointed to a MW 310 compound; $[M+Li]^+$ at m/z 317 was observed. The molecular formula was determined by exact mass measurement of the molecular ion:

Calculated for $C_{17}H_{26}O_5$: 310.1780. Found: 310.1778.

The compound formed a tri-TMS derivative.

EXAMPLE 5

Typical Pharmaceutical Compositions

A: Dry Filled Capsules Containing 50 mg of Active Ingredient Per Capsule

| Ingredient | Amount per capsule (mg) |
|---|---|
| Compound A | 50 |
| Lactose | 149 |
| Magnesium stearate | 1 |
| Capsule (size No. 1) | 200 |

Compound A can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain Compound A (25 mg), pregelatinized starch USP (82 mg), microcrystalline cellulose (82 mg), and magnesium stearate (1 mg).

C: Combination Tablet

A typical combination tablet would contain a diuretic such as hydrochlorothiazide (25 mg) and Compound A (50 mg) pregelatinized starch USP (82 mg), microcrystalline cellulose (82 mg) and magnesium stearate (1 mg).

D: Suppository

Typical suppository formulations for rectal administration can contain Compound A (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation may contain Compound A (30 mg,) sodium phosphate dibasic anhydrous (11.4 mg), benzyl alcohol (0.01 ml), and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of the formula

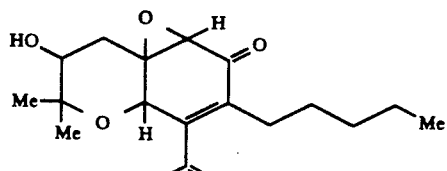

A

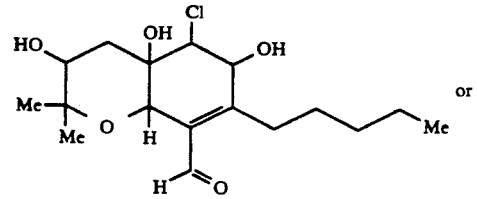

B or

-continued

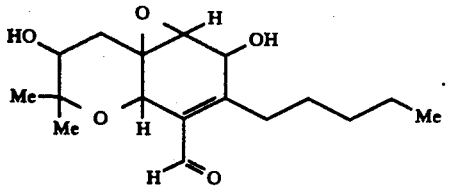

2. A pharmaceutical composition useful in the treatment of hypertension which comprises a pharmaceutically acceptable carrier and a therapeutically effective amount of a compound of claim 1.

3. A method of treating hypertension which comprises administering to a patient in need of such treatment a therapeutically effective amount of a compound of claim 1.

4. A method for reducing the undesirable clinical manifestations of angiotensin II binding activity comprising administering a therapeutic amount of a compound of the formula

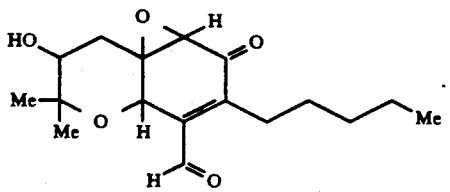

A

* * * * *